(12) United States Patent
Tanida

(10) Patent No.: US 7,367,225 B2
(45) Date of Patent: May 6, 2008

(54) APPARATUS FOR MEASURING MECURY CONTAINED IN GASEOUS MEDIUM

(75) Inventor: Koji Tanida, Takatsuki (JP)

(73) Assignee: Nippon Instruments Corporation, Osaka (JP)

( * ) Notice: Subject to any disclaimer, the term of this patent is extended or adjusted under 35 U.S.C. 154(b) by 339 days.

(21) Appl. No.: 11/305,259

(22) Filed: Dec. 19, 2005

(65) Prior Publication Data
US 2006/0137433 A1   Jun. 29, 2006

(30) Foreign Application Priority Data
Dec. 28, 2004   (JP) ............................. 2004-381437

(51) Int. Cl.
G01N 33/00   (2006.01)
(52) U.S. Cl. .................................. 73/61.41
(58) Field of Classification Search ............... 73/61.41, 73/23.2, 53.01
See application file for complete search history.

(56) References Cited

U.S. PATENT DOCUMENTS

| 4,141,701 | A | * | 2/1979 | Ewan et al. ................... 95/217 |
| 5,277,871 | A |   | 1/1994 | Fujii et al. |
| 5,567,621 | A |   | 10/1996 | Tahara et al. |
| 6,013,158 | A | * | 1/2000 | Wootten ....................... 202/99 |
| 6,210,467 | B1 | * | 4/2001 | Howard ........................ 95/172 |
| 2004/0244382 | A1 | * | 12/2004 | Hagen et al. .................. 60/775 |
| 2005/0056313 | A1 | * | 3/2005 | Hagen et al. .................. 137/3 |

FOREIGN PATENT DOCUMENTS

| EP | 1489412 A1 | 12/2004 |
| JP | 2004-354067 | 12/2004 |

* cited by examiner

Primary Examiner—Herzon Williams
Assistant Examiner—Rodney Frank
(74) Attorney, Agent, or Firm—Sughrue Mion, PLLC

(57) ABSTRACT

To provide a highly reliable apparatus for measuring mercury contained in the gaseous medium, in which the outlet port 3b of the reducing tube and the gas-liquid separator, both susceptible to deposition of stain, can be automatically cleaned to avoid reduction of the sensitivity of the measuring instrument, the apparatus for measuring mercury contained in the gaseous medium includes a reducing tube 3 for reducing divalent mercury contained in a gaseous medium to zerovalent mercury, a gas-liquid separator 4 for removing a liquid component (drain) from the gaseous medium that has passed through the reducing tube 3, a measuring instrument 6 for measuring the quantity of the mercury contained in the gaseous medium delivered from the gas-liquid separator 4, and a cleaning system 10 for running a cleaning liquid from an outlet port of the reducing tube 3 past the gas-liquid separator 4 to emerge outwardly of the gas-liquid separator 4.

5 Claims, 2 Drawing Sheets

APPARATUS FOR MEASURING MECURY CONTAINED IN GASEOUS MEDIUM

BACKGROUND OF THE INVENTION

1. Field of the Invention

The present invention relates to an apparatus for measuring mercury contained in the gaseous medium for measuring the quantity of mercury contained in exhaust gases emitted from a chemical plant such as, for example, fossil fuel burning facilities, waste incinerators or chemical processes and, more particularly, to an automatic cleaning of the apparatus for measuring the quantity of mercury contained in a gaseous medium.

2. Description of the Prior Art

Mercury contained in various exhaust gases emitted from a chemical plant such as, for example, fossil fuel burning facilities, waste incinerators and chemical processes is generally found in two chemical forms; zerovalent mercury ($Hg^0$) such as metal mercury, and divalent mercury ($Hg^{2+}$). Of them, the metal mercury is difficult to dissolve in water and is apt to diffuse into the atmosphere, constituting a cause of atmospheric pollution. On the other hand, the divalent mercury is easy to dissolve in water and does often constitute a cause of soil contamination.

As discussed above, metal mercury and divalent mercury contained in the exhaust gases brings adverse influence on the environment and, therefore, the apparatus for measuring mercury contained in the gaseous medium is disposed in, for example, a wall defining a flue (or pipe) of the burning facilities and chemical plants so that the quantity of mercury contained in the exhaust gases can be monitored at all times.

The apparatus for measuring mercury contained in the gaseous medium referred to above includes a gas introducing passage fluid connected in parallel to the flue and is connected, in the order from the flue in a downstream direction, with a reducing tube (reducing column) filled with a reducing catalyst for reducing divalent mercury ($Hg^{2+}$) contained in the gaseous medium to metal mercury ($Hg^0$), a gas-liquid separator for removing a moisture component contained in the gaseous medium, a dehumidifier equipped with a drain pump, an interfering component removal column for removing an interfering component such as, for example, sulfuric dioxide, and a mercury measuring instrument for measuring the concentration of metal mercury ($Hg^0$) that has passed through the reducing column. The reducing tube referred to above allows the metal mercury ($Hg^0$), reduced from the divalent mercury ($Hg^{2+}$), and the metal mercury ($Hg^0$), initially contained in the gaseous medium, to pass therethrough.

With this measuring device, the divalent mercury ($Hg^{2+}$), which could not be measured in the form as it stands, can be reduced to the metal mercury ($Hg^0$) that can be measured and, therefore, the total quantity of mercury contained in the exhaust gases can be measured. See, for example, the Japanese Laid-open Patent Publication No. 2004-354067.

It has, however, been found that the conventional apparatus for measuring mercury of a type referred to above has the following problem. Specifically, since the reducing tube filled with the reducing catalyst is surrounded with and is therefore heated by a heating device such as, for example, a heater for the purpose of facilitating the functionality of the catalyst filled therein, stain such as snoot does not easily deposit, but is apt to deposit within an outlet port of the reducing tube, at which temperature decreases as compared with that at upper and intermediate portions of the reducing tube, and within the gas-liquid separator. If the outlet port of the reducing tube and the gas-liquid separator are allowed to stand without the stain being removed, the mercury will be adsorbed in those portions thereof where stain deposited. Once this occurs, the adsorbed mercury will lead to a measurement error which would eventually lower the sensitivity of the measuring instrument for measuring the quantity of mercury contained in gaseous medium, with the reliability of the apparatus for measuring mercury lowered consequently.

SUMMARY OF THE INVENTION

In view of the foregoing, the present invention has for its primary object to provide a highly reliable apparatus for measuring mercury contained in the gaseous medium, in which the outlet port of the reducing tube and the gas-liquid separator, both susceptible to deposition of stain, can be automatically cleaned to avoid reduction of the sensitivity of the measuring instrument.

In order to accomplish the foregoing object, the apparatus for measuring mercury contained in the gaseous medium of the present invention comprises a reducing tube for reducing divalent mercury contained in a gaseous medium to zerovalent mercury (i.e., metal mercury), a gas-liquid separator for removing a liquid component from the gaseous medium that has passed through the reducing tube, a measuring instrument for measuring the quantity of the mercury contained in the gaseous medium delivered from the gas-liquid separator, and a cleaning system for running a cleaning liquid from an outlet port of the reducing tube past the gas-liquid separator to emerge outwardly of the gas-liquid separator.

According to the present invention, a flow passage portion from the outlet port of the reducing tube to the gas-liquid separator, which is so susceptible to contamination as to lead to a measurement error, can be cleaned with the cleaning liquid running within the cleaning system and, therefore, contaminant then deposited inside that flow passage portion can be removed and transported by the cleaning liquid to the outside of the gas-liquid separator. Accordingly, there is no possibility that flow passage portion running from the outlet port of the reducing tube to the gas-liquid separator will be constantly contaminated with stains and, therefore, the measurement error resulting from adsorption of mercury on the stained portions in that flow passage portion can advantageously be eliminated, allowing the apparatus for measuring mercury contained in the gaseous medium to provide a high reliability and also to provide a stabilized measurement result for a substantial period of time. Also, since the apparatus for measuring mercury contained in the gaseous medium embodying the present invention can be obtained merely by adding the cleaning system and a concomitant pump to any existing apparatus for measuring mercury contained in the gaseous medium, it can easily be manufactured.

In a preferred embodiment of the present invention, the cleaning system may include a supply pump for supplying the cleaning liquid to the gas-liquid separator and a delivery pump for delivering a liquid component from the gas-liquid separator.

According to this embodiment, the cleaning liquid to be supplied to the gas-liquid separator is supplied by the supply pump under a predetermined pumping pressure to achieve a high pressure cleaning and, therefore, contaminant depositing in that flow passage portions from the outlet port of the reducing tube to the gas-liquid separator can be forcibly removed. On the other hand, the cleaning liquid supplied to the gas-liquid separator and containing the contaminant removed therefrom can be smoothly delivered outwardly.

In another preferred embodiment of the present invention, the cleaning system may also includes a cleaning controller for activating intermittently. This cleaning controller is utilized to intermittently activate, for example, the supply pump.

The use of the cleaning controller is particularly advantageous in that since the cleaning system is intermittently activated based on a setting of the cleaning controller, the length of time during which the cleaning system is activated and the timing at which the cleaning system is activated can be properly set in dependence on the extent to which that flow passage portion is contaminated, thus accomplishing an efficient removal of the deposited contaminant.

In a further preferred embodiment of the present invention, the apparatus for measuring mercury contained in the gaseous medium of the present invention also includes a heating instrument for the reducing tube and a cooling unit for cooling and dehumidifying a gaseous medium flowing from the gas-liquid separator.

According to this embodiment, when the reducing tube is heated by the heating instrument, a reducing catalyst filled in such reducing tube can be heated with its activity maintained consequently. Also, since the gaseous medium flowing from the gas-liquid separator is cooled and then dehumidified, heat of the gaseous medium and a liquid component will not interfere with the measuring instrument in the subsequent stage and, therefore, the quantity of the mercury (i.e., metal mercury) can be measured with high precision.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
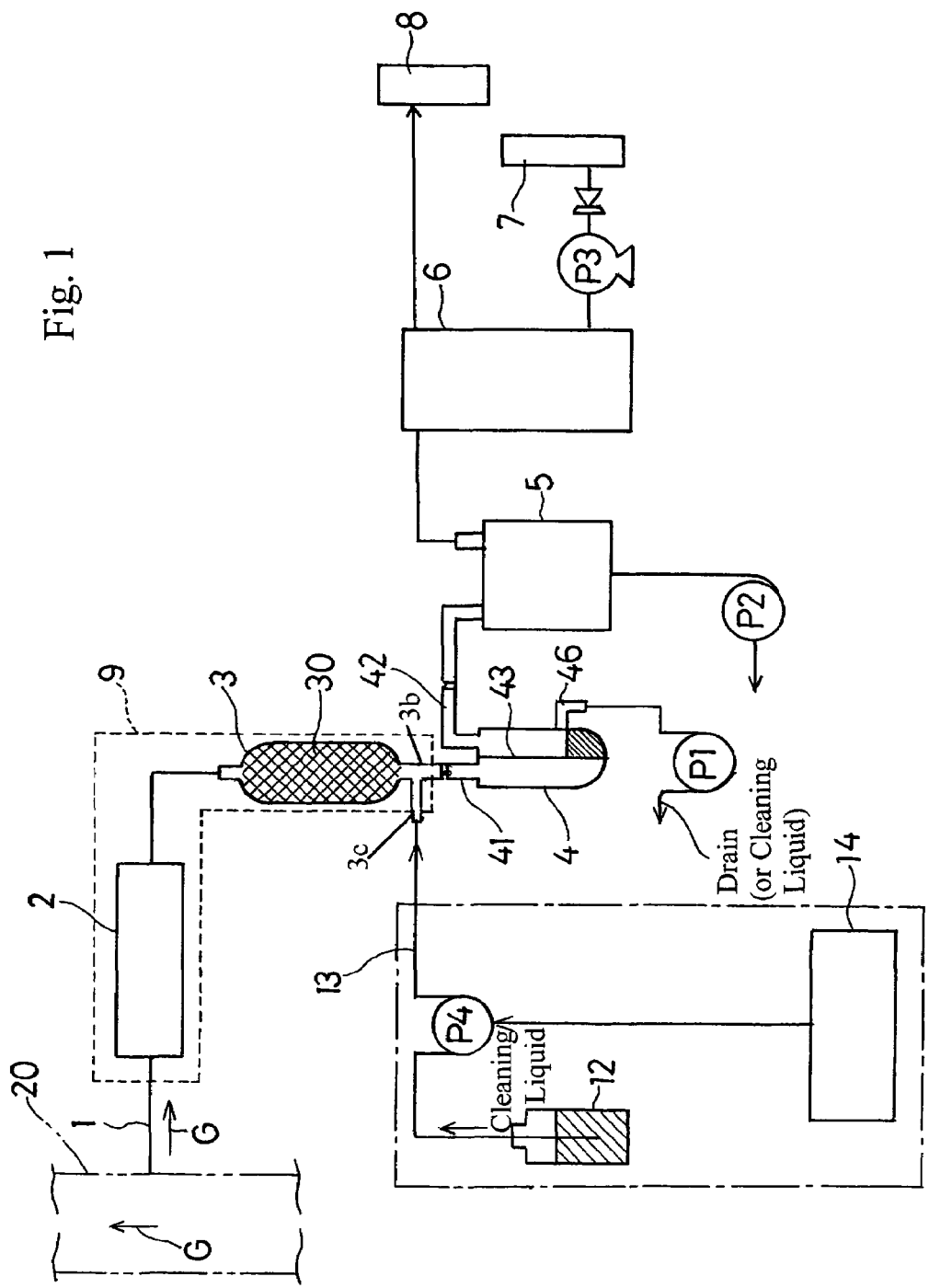
FIG. 1 is a system diagram showing a apparatus for measuring mercury contained in gaseous medium according to a preferred embodiment of the present invention.

Hereinafter, a preferred embodiment of the present invention will be described in detail with reference to the accompanying drawings. FIG. 1 is a system diagram showing a apparatus for measuring mercury contained in the gaseous medium according to the preferred embodiment of the present invention. The apparatus for measuring mercury contained in the gaseous medium shown therein is used in the form as fitted to a side wall of a flue (pipe) 20 in, for example, a chemical plant for the flow of exhaust gases. As shown therein, a gas introducing passage 1 is fluid connected with the side wall of the flue 20 and, in the order from the flue 20 in a downstream direction, the gas introducing passage 1 is fluid connected with a dust filter 2 for removing dust contained in a gaseous medium G, a reducing tube 3 filled with a reducing catalyst 30 for reducing divalent mercury ($Hg^{2+}$) contained in the gaseous medium G to metal mercury ($Hg^0$), and a gas-liquid separator 4 for removing a liquid component (drain) from the gaseous medium G which has passed through the reducing tube 3. The gas-liquid separator 4 is fluid connected with a delivery pump P1 (such as, for example, a peristaltic pump).

A cooling unit 5 is fluid connected with a downstream side of the gas-liquid separator 4 and is on the other hand connected with a mercury measuring instrument 6 for measuring the quantity of mercury (as metal mercury ($Hg^0$)) contained in the gaseous medium G, a suction pump P3 for introducing the gaseous medium G from the flue 20 to the gas introducing passage 1, a gas flow controller 7 for setting a flow rate of the gaseous medium G being introduced by the suction pump P3, and a monitor 8 for providing a visual indication of a result of measurement performed by the mercury measuring instrument 6. The cooling unit 5 is fluid connected with a drain pump P2 for delivering the drain.

For the reducing catalyst 30 filled in the reducing tube 3, tin chloride ($SnCl_2$) having an excellent power of reducing the divalent mercury ($Hg^{2+}$), for example, can be suitably employed. Also, the dust filter 2 and the reducing tube 3 are accommodated within a heating instrument 9 such as a heater and the temperature thereof is controlled by an unillustrated control device to a predetermined value. Accordingly, the activity of the reducing catalyst 30 can be maintained.

Figure 2:
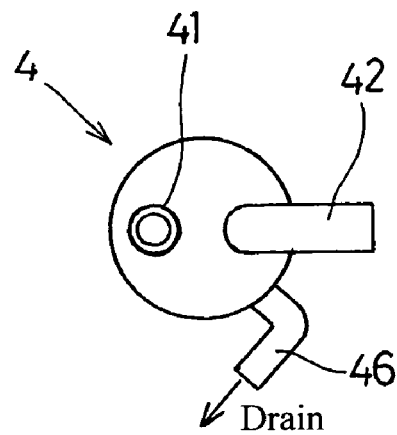
FIG. 2 is a schematic plan view of a gas-liquid separator employed in the apparatus for measuring mercury contained in the gaseous medium shown in FIG. 1.
Figure 3:
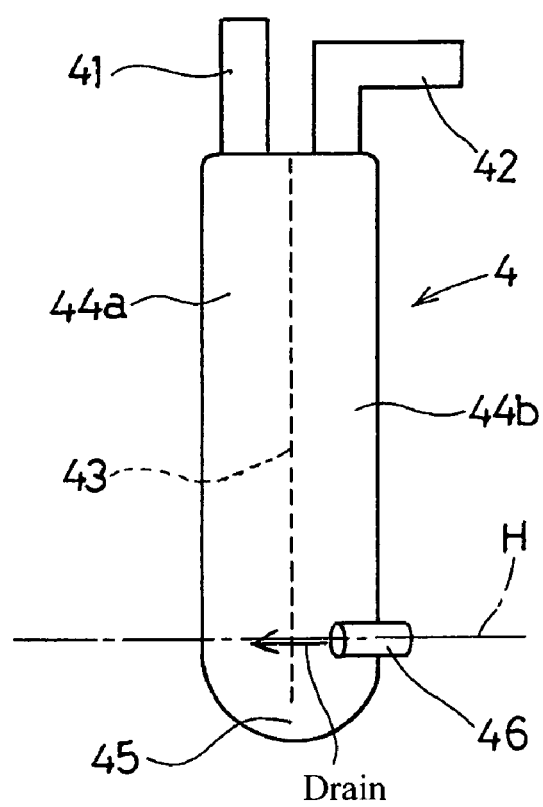
FIG. 3 is a schematic front elevational view of the gas-liquid separator shown in FIG. 2.

The gas-liquid separator 4 is made of a heat resisting glass (such as, for example, "Pyrex" trademarked glass) and has such a specific structure as shown in FIGS. 2 and 3 which show a plan view and an elevational view, respectively. As best shown in FIG. 3, the gas-liquid separator 4 has an upper portion provided with an introducing pipe 41, which is communicated with an outlet port 3b of the reducing tube 3 for receiving the gaseous medium G from the reducing tube 3 into the gas-liquid separator 4, and a delivery pipe 42 which is communicated with the cooling unit 5 for delivering the gaseous medium G from the gas-liquid separator 4 to the cooling unit 5. The gas-liquid separator 4 has its interior divided into left and right chambers 44a and 44b by a partition plate 43 made of a gas permeable material, which chambers 44a and 44b are communicated with each other through a perforation 45 defined in a lower portion of the partition plate 43. At a predetermined height level, shown by the broken line H, from the bottom of the gas-liquid separator 4, a drain pipe 46 is provided in the gas-liquid separator 4 and, therefore, the drain separated within the gas-liquid separator 4 can be discharged to the outside through the drain pipe 46 when the quantity of the drain accumulated within the gas-liquid separator 4 exceeds the height level shown by the broken line H.

To the apparatus for measuring mercury contained in the gaseous medium of the structure described above, a cleaning system 10 is added as shown in FIG. 1 for cleaning the outlet port 3b of the reducing tube 3 and the gas-liquid separator 4. Specifically, this cleaning system 10 includes a reservoir tank 12 containing a quantity of cleaning liquid, a cleaning liquid supply passage 13 for supplying the cleaning liquid within the reservoir tank 12 to a site between the reducing catalyst 30 within the reducing tube 3 and gas-liquid separator 4 and upstream of the outlet port 3b of the reducing tube 3, a supply pump P4 (such as, for example, a peristaltic pump) disposed on the cleaning liquid supply passage 13, and a cleaning controller 14 for controlling the supply pump P4.

The supply pump P4 is controlled by the cleaning controller 14 so as to be driven intermittently so that the cleaning liquid can be supplied under a predetermined pressure for, for example, 5 minutes per hour from a flow passage portion including an inlet port 3c for cleaning liquid of the outlet port side of the reducing tube 3, that is, a passage downstream of the reducing catalyst 30 and the gas-liquid separator 4 to accomplish a high pressure cleaning. Accordingly, contaminant such as snoot deposited in that flow passage portion ranging from the outlet port 3b of the reducing tube 3 to the gas-liquid separator 4 can be forcibly removed. The cleaning liquid containing the removed contaminant is subsequently discharged by the drive of the delivery pump P1 from the drain pipe 46 of the gas-liquid separator 4 to the outside thereof.

Hereinafter, the measurement of the quantity of mercury with the apparatus for measuring mercury contained in the gaseous medium of the structure described above and the automatic cleaning performed therein will now be described. It is, however, to be noted that the sequence of operation of the apparatus for measuring mercury contained in the gaseous medium as hereinafter set forth is carried out under the control of the unillustrated control device. In the first place, when the suction pump P3 is driven by the gas flow controller 7, a gaseous medium G is introduced at a predetermined flow rate from the flue 20 into the gas introducing passage 1 and is then sampled. The gaseous medium G so introduced into the gas introducing passage 1 is subsequently passed through the dust filter 2, by which dust contained in the gaseous medium G is removed, and is then supplied to the reducing tube 3. As the gaseous medium G flows through the reducing tube 3, the divalent mercury ($Hg^{2+}$) contained in the gaseous medium G is reduced to the metal mercury ($Hg^0$) by the reducing catalyst filled in the reducing tube 3, and the gaseous medium G containing both of the metal mercury ($Hg^0$), reduced from the divalent mercury ($Hg^{2+}$), and the metal mercury ($Hg^0$), initially contained in the gaseous medium, is subsequently introduced into the gas-liquid separator 4.

In the gas-liquid separator 4, not only is a liquid component (drain) contained in the gaseous medium G removed, but also a small quantity of divalent mercury ($Hg^{2+}$) dissolved in the drain is evaporated and reduction thereof is accelerated. The drain removed in the gas-liquid separator 4 is discharged by the delivery pump P1, shown in FIG. 1, to the outside when such drain exceeds the height level H of the drain pipe 46 to overflow.

Thereafter, the gaseous medium G past the gas-liquid separator 4 is supplied to the cooling unit 5, at which the drain produced as a result of cooling and dehumidification is discharged by the delivery pump P2 to the outside. The gaseous medium G of a temperature reduced down to a value appropriate for the measurement of the mercury contained in the gaseous medium as a result of the cooling and dehumidification is supplied to the mercury measuring instrument 6, by which the concentration of the metal mercury ($Hg^0$) is continuously measured, and the result of this measurement is displayed on the monitor 8 on a real time basis.

The gas-liquid separator 4 referred to above is provided with a reverse flow preventing structure. More specifically, since the flue 20 is generally held under a negative pressure (lower than the atmospheric pressure), the drain and the gaseous medium G will flow in a reverse direction within the measuring system when the suction pump P3 is halted upon completion of the measurement or suspension of the measurement. However, since the chambers 44a and 44b within the gas-liquid separator 4 are communicated with each other through the perforation 45 as shown and described with reference to FIG. 3, the reverse flow of the drain within the gas-liquid separator 4 is suppressed, thereby achieving prevention of the reverse flow within the measuring system.

As the measurement of the mercury with this apparatus for measuring mercury contained in the gaseous medium continues, stains are deposited in the outlet port 3b of the reducing tube 3 and the gas-liquid separator 4 with passage of time and, accordingly, each time the apparatus for measuring mercury contained in the gaseous medium is operated for a predetermined length of time, the cleaning system 10 is intermittently activated (for, for example, 5 minutes per hour) by a command from the cleaning controller 14. When the cleaning system 10 is so activated while the suction pump P3 is kept driven, the cleaning liquid flows under a predetermined pressure continuously for a predetermined length of time from the reservoir tank 12 into the gas-liquid separator 4 through the introducing pipe 41 via the inlet port 3c for cleaning liquid and the outlet port 3b of the reducing tube 3, so that a flow passage portion running from the outlet port 3b of the reducing tube 3 to the gas-liquid separator 4 is automatically cleansed at high pressure. By this high pressure cleaning, the stains such as snoot deposited in the outlet port 3b of the reducing tube 3, which forms a passage downstream of the reducing catalyst 30, and the gas-liquid separator 4 are removed and flushed out and are then discharged by the delivery pump P1 from the drain pipe 46 of the gas-liquid separator 4 to the outside.

As hereinbefore described, according to the apparatus for measuring mercury contained in the gaseous medium of the present invention, that flow passage portion running from the outlet port of the reducing tube to the gas-liquid separator, which is susceptible to deposition of contaminant that leads to the measurement error as a result of adsorption of mercury, can be automatically cleansed at high pressure with the cleaning liquid supplied through the cleaning system with the contaminant removed consequently. Accordingly, since there is no possibility of constant contamination of that flow passage portion running from the outlet port of the reducing tube 3 to the gas-liquid separator 4, it is possible to eliminate a measurement error resulting from adsorption of mercury on the contaminated areas within that flow passage portion and, therefore, the measuring reliability of the apparatus for measuring mercury contained in the gaseous medium can be increased and the stabilized measurement result can be obtained for a substantial length of time.

Also, since the apparatus for measuring mercury contained in the gaseous medium of the present invention is of a simplified structure, in which any existing apparatus for measuring mercury contained in the gaseous medium is added with the cleaning system 10 and the concomitant pumps P1 and P4, the manufacture thereof can easily be accomplished. In addition, in dependence on the extent to which that flow passage portion running from the outlet port of the reducing tube 3 to the gas-liquid separator 4, which may vary from one kind of the gaseous medium G introduced to another, is contaminated, a proper operation can be performed such as the length of time during which the cleaning system is activated and the timing at which the cleaning system is activated, both set by the cleaning controller 14, and, hence, the deposited contaminant can be efficiently removed. Yet, since the cleaning system 10 suffices to be intermittently activated, measurement with the apparatus for measuring mercury contained in the gaseous medium will not be disturbed.

The present invention having been fully described hereinbefore, it has now become clear that in the apparatus for measuring mercury contained in the gaseous medium of the present invention the contaminant within the flow passage portion running from the outlet port of the reducing tube to the gas-liquid separator is removed by cleaning and adsorption of mercury in the contaminated areas within that flow passage portion, which least to the measurement error, is also eliminated. Therefore, not only can the reliability of the apparatus for measuring mercury contained in the gaseous medium be increased, but also the stabilized measurement result can be obtained for a substantial length of time. In addition, since the apparatus for measuring mercury contained in the gaseous medium of the present invention can be obtained merely by adding the cleaning system and the concomitant pumps to any existing apparatus for measuring mercury contained in the gaseous medium, it is quite easy to manufacture such mercury measuring device.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. Apparatus for measuring mercury contained in a gaseous medium, which comprises:

a reducing tube for reducing divalent mercury contained in a gaseous medium to zerovalent mercury;

a gas-liquid separator for removing a liquid component from the gaseous medium that has passed through the reducing tube;

a measuring instrument for measuring the quantity of the mercury contained in the gaseous medium delivered from the gas-liquid separator; and a cleaning system for running a cleaning liquid from an outlet port of the reducing tube past the gas-liquid separator to emerge outwardly of the gas-liquid separator.

2. The apparatus for measuring mercury contained in the gaseous medium as claimed in claim 1, wherein the cleaning system includes a supply pump for supplying the cleaning liquid to the gas-liquid separator and a delivery pump for delivering a liquid component from the gas-liquid separator.

3. The apparatus for measuring mercury contained in the gaseous medium as claimed in claim 1, wherein the cleaning system includes a cleaning controller for activating intermittently.

4. The apparatus for measuring mercury contained in the gaseous medium as claimed in claim 3, wherein the cleaning controller is operable to intermittently drive the supply pump.

5. The apparatus for measuring mercury contained in the gaseous medium as claimed in claim 1, further comprising a heating instrument for the reducing tube and a cooling unit for cooling and dehumidifying the gaseous medium flowing from the gas-liquid separator.

* * * * *

UNITED STATES PATENT AND TRADEMARK OFFICE
CERTIFICATE OF CORRECTION

PATENT NO. : 7,367,225 B2  Page 1 of 1
APPLICATION NO. : 11/305259
DATED : May 6, 2008
INVENTOR(S) : Koji Tanida It is certified that error appears in the above-identified patent and that said Letters Patent is hereby corrected as shown below:

On The Title Page (54) and on Column 1, Line 1:

Please delete: "Mecury" and insert: --Mercury--

Signed and Sealed this

Twenty-sixth Day of August, 2008

JON W. DUDAS
*Director of the United States Patent and Trademark Office*